US011883680B2

(12) United States Patent
McCormack et al.

(10) Patent No.: US 11,883,680 B2
(45) Date of Patent: Jan. 30, 2024

(54) METHOD AND APPARATUS FOR TIGHTENING SKIN AND OTHER TISSUES

(71) Applicant: The General Hospital Corporation, Boston, MA (US)

(72) Inventors: Michael McCormack, Medford, MA (US); Robert Redmond, Newton Centre, MA (US); William Gerald Austen, Jr., Weston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/660,536

(22) Filed: Apr. 25, 2022

(65) Prior Publication Data

US 2022/0241607 A1 Aug. 4, 2022

Related U.S. Application Data

(62) Division of application No. 16/079,793, filed as application No. PCT/US2017/019321 on Feb. 24, 2017, now Pat. No. 11,400,310.
(Continued)

(51) Int. Cl.
*A61N 5/06* (2006.01)
*A61B 18/20* (2006.01)
(Continued)

(52) U.S. Cl.
CPC ............ *A61N 5/062* (2013.01); *A61B 18/203* (2013.01); *A61B 2017/00765* (2013.01);
(Continued)

(58) Field of Classification Search
CPC ................. A61N 5/062; A61N 5/0616; A61N 2005/0652; A61N 2005/0663;
(Continued)

(56) References Cited

U.S. PATENT DOCUMENTS 7,073,510 B2 7/2006 Redmond et al.
7,918,814 B2 4/2011 Prausnitz et al.
(Continued)

FOREIGN PATENT DOCUMENTS

CN 102176877 A 9/2011
CN 103153396 A 6/2013
(Continued)

OTHER PUBLICATIONS

Wikipedia, Syringe, https://en.wikipedia.org/wiki/Syringe, Dec. 3, 2015, 9 pages.
(Continued)

*Primary Examiner* — Dung T Ulsh
(74) *Attorney, Agent, or Firm* — Quarles & Brady LLP

(57) ABSTRACT

A system and method for treating a tissue is provided. The treatment causes a tightening or lifting of tissue. The method includes delivering a photochemical agent through a depth of the tissue to distribute the photochemical agent adjacent proteins within the tissue and irradiating the tissue with an electromagnetic irradiation at a wavelength that activates the photochemical agent, causing a protein response that brings fibers of the tissue closer together in order to one of reduce tissue laxity and tighten the tissue. A kit is provided to facilitate the method.

14 Claims, 3 Drawing Sheets

Related U.S. Application Data

(60) Provisional application No. 62/299,853, filed on Feb. 25, 2016.

(51) Int. Cl.
*A61B 17/00* (2006.01)
*A61B 18/00* (2006.01)
*A61N 5/067* (2006.01)
*A61K 41/00* (2020.01)

(52) U.S. Cl.
CPC ............... *A61B 2018/0047* (2013.01); *A61B 2018/00559* (2013.01); *A61K 41/0071* (2013.01); *A61N 5/067* (2021.08); *A61N 5/0616* (2013.01); *A61N 2005/0652* (2013.01); *A61N 2005/0663* (2013.01)

(58) Field of Classification Search
CPC ............ A61N 2005/067; A61B 18/203; A61B 2017/00765; A61B 2018/0047; A61B 2018/00559; A61K 41/0071
See application file for complete search history.

(56) References Cited

U.S. PATENT DOCUMENTS

| | | | |
|---|---|---|---|
| 8,092,490 B2 | 1/2012 | Redmond et al. | |
| 9,511,034 B1 | 12/2016 | Garrett | |
| 10,555,754 B2 | 2/2020 | Ginggen et al. | |
| 2007/0219605 A1 | 9/2007 | Yaroslavsky et al. | |
| 2008/0214987 A1 | 9/2008 | Xu | |
| 2009/0069741 A1 | 3/2009 | Altshuler et al. | |
| 2009/0098102 A1* | 4/2009 | Cho | A61Q 19/00 424/94.63 |
| 2010/0312167 A1 | 12/2010 | Castro | |
| 2012/0226214 A1* | 9/2012 | Gurtner | A61B 18/203 602/53 |
| 2013/0023966 A1 | 1/2013 | Depfenhart et al. | |
| 2013/0345616 A1 | 12/2013 | Chang | |
| 2014/0025033 A1 | 1/2014 | Mirkov et al. | |
| 2014/0039523 A1 | 2/2014 | Austen | |
| 2014/0323907 A1* | 10/2014 | Frazier | A61M 5/00 604/93.01 |
| 2015/0134049 A1 | 5/2015 | Austen, Jr. et al. | |
| 2015/0320595 A1 | 11/2015 | Blumenkranz et al. | |
| 2015/0320990 A1* | 11/2015 | Burton | A61M 5/1454 604/173 |
| 2015/0366719 A1 | 12/2015 | Evinson et al. | |
| 2016/0192961 A1 | 7/2016 | Ginggen et al. | |
| 2017/0361131 A1 | 12/2017 | Greaves | |

FOREIGN PATENT DOCUMENTS

| | | |
|---|---|---|
| WO | 03059144 A2 | 7/2003 |
| WO | 2013063530 A2 | 5/2013 |
| WO | 2014008470 A1 | 1/2014 |
| WO | 2014008481 A1 | 1/2014 |
| WO | 2014099404 A1 | 6/2014 |
| WO | 2015021434 A2 | 2/2015 |

OTHER PUBLICATIONS

Wikipedia, Hypodermic Needle, https://en.wikipedia.org/wiki/Hypodermic_needle, Jan. 5, 2016, 5 pages.
China National Intellectual Property Administration, First Office Action and Search Report, Application No. 201780013733.0, dated Sep. 3, 2020, 15 pages.
China National Intellectual Property Administration, Second Office Action and Search Report, Application No. 201780013733.0, dated Apr. 21, 2021, 27 pages.
European Patent Office, Extended Search Report, Application No. 17757285.6, dated Oct. 9, 2019, 8 pages.
European Patent Office, Communication, Application No. 17757285.6, dated Feb. 25, 2022, 5 pages.
Japan Patent Office, Notification of Reasons for Refusal, Application No. 2018-544795, dated Mar. 16, 2021, 5 pages.
Japan Patent Office, Notification of Reasons for Refusal, Application No. 2018-544795, dated Nov. 9, 2021, 6 pages.
PCT International Search Report and Written Opinion, PCT/US2017/019321, dated May 19, 2017, 14 pages.

* cited by examiner

METHOD AND APPARATUS FOR TIGHTENING SKIN AND OTHER TISSUES

CROSS-REFERENCE TO RELATED APPLICATIONS

This application is a divisional of U.S. application Ser. No. 16/079,793 filed on Aug. 24, 2018, which is a U.S. National Phase of PCT Application No. PCT/US2017/019321 filed on Feb. 24, 2017 which is based on, claims priority to, and incorporates herein by reference in its entirety, U.S. Provisional Patent Application Ser. No. 62/299,853, filed on Feb. 25, 2016, and entitled "Method and Apparatus for Tightening Skin and Other Tissues.

BACKGROUND

Over one quarter of the US population suffers from age-related changes in skin appearance and this number is expected to rise as the population ages. Furthermore, eight percent of the US population receives treatments to reduce skin laxity. For example, in 2013, over 1.5 million related procedures were performed in the US. These types of procedures collectively cost over six billion dollars annually, accounting for half of the US aesthetic market. Despite the large market, however, the side effects of current treatments limit market growth.

Currently, surgery represents the gold standard to reduce skin laxity, but is invasive, costly, and inconvenient. Minimally invasive energy-based platforms offer an alternative to surgery, but are complicated with their own side effects. For example, present surgery alternatives like laser, radiofrequency, and ultrasound rely on devices that cause thermal damage to the tissue area being treated. This causes significant recovery time, delayed re-epithelialization, prolonged erythema, hypo- and hyper-pigmentation and, in some instances, scarring. Additionally, these surgery alternatives produce only modest efficacy after multiple treatments, have high patient-to-patient variability, and suffer from a significant non-responder rate. Other reported side effects include significant pain, bruising, tenderness, swelling, scabbing, and blistering.

Beside physical side effects, economic issues also hinder market growth. In particular, surgery is costly and requires treatments to be performed by a physician in an operating room. Additionally surgery alternatives generally require costly capital equipment, which limits market acceptance, revenue potential, and profitability.

Therefore, there exists a clinical need for a safe and effective treatment for reducing skin laxity and/or tightening other tissue types that is minimally invasive, convenient, and offers minimal downtime.

SUMMARY

The systems and methods of the present disclosure overcome the above and other drawbacks by providing a non-invasive, fluence-based system and method for crosslinking as a means for bringing collagen or structural proteins of a tissue closer together, effectively reducing volume and "tightening" the tissue.

In accordance with one aspect of the disclosure, a method for tightening or lifting a tissue is provided. The method includes delivering a photochemical agent through a depth of the tissue to distribute the photochemical agent adjacent proteins within the tissue, and irradiating the tissue with an electromagnetic radiation source at a wavelength that activates the photochemical agent, causing a protein response that brings fibers of the tissue closer together in order to one of reduce laxity and tighten the tissue.

In the above method, the delivery step can include puncturing through a surface of the tissue to create access below the surface to the collagen within the tissue and applying a photochemical agent to the surface so that the photochemical agent penetrates the puncture holes and distributes throughout a depth of the tissue adjacent the proteins within the tissue. Alternatively, the delivery step can include inserting a needle into the tissue and simultaneously pulling the needle out of the tissue while injecting the photochemical agent through the needle so that the photochemical agent penetrates a depth of the tissue. Additional or similar delivery steps can be used.

In accordance with another aspect of the disclosure, a kit for treating tissue using with an electromagnetic radiation source is provided. The kit includes a needle sized to create puncture holes in the tissue and a photochemical agent configured to penetrate through the puncture holes when applied to the tissue and to be activated to cause crosslinking of proteins in the tissue when irradiated with a predetermined electromagnetic radiation.

The foregoing and other advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The disclosure provides a system and method for tightening skin and other tissue through photochemical crosslinking of tissue collagen and other structural proteins. The system includes a mechanism to transdermally deliver a photochemical agent into the target tissue, and an energy source system to uniformly and controllably irradiate the target tissue with electromagnetic radiation. The energy source may include an electromagnetic radiation source that activates the photochemical agent, which causes collagen crosslinking and, in effect, tightens the target tissue. This photochemical tissue tightening system and method can be used instead of surgery to directionally tighten or lift tissue without incurring the risks and side effects associated with existing surgery alternatives.

Figure 1:
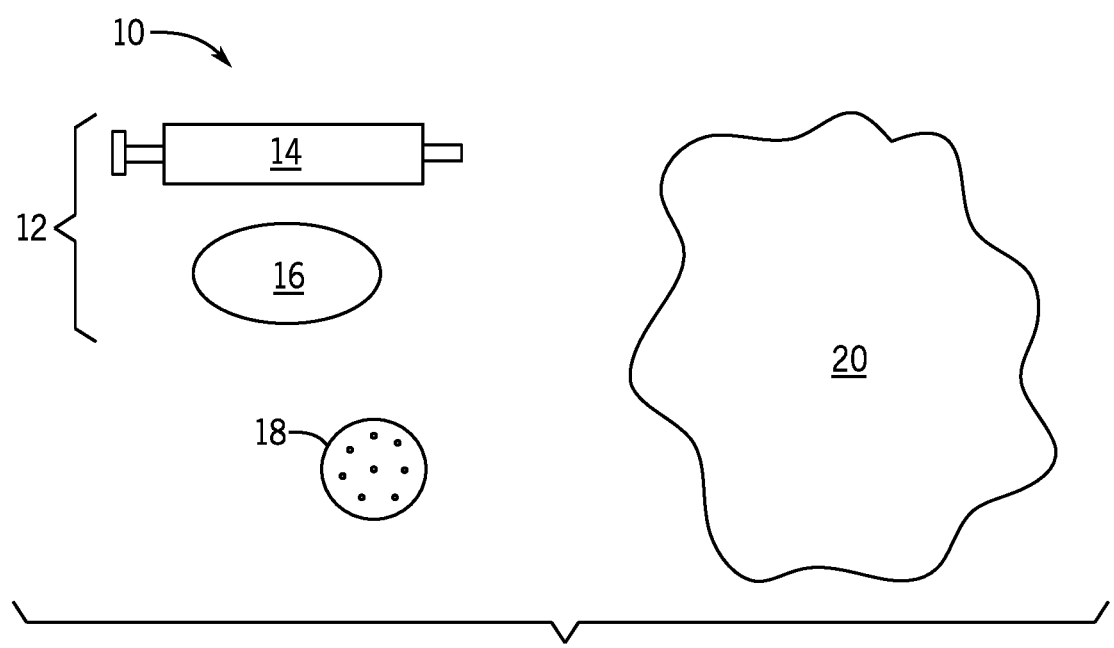
FIG. 1 is a schematic view of a system for tightening a target tissue.

FIG. 1 is a schematic view of a tissue tightening system 10 according to one aspect of the disclosure. The system 10 generally includes a delivery mechanism 12, including a needle 14 and/or an applicator 16, and an electromagnetic radiation source 18. The electromagnetic radiation source 18 may include a light-emitting system, such as a light emitting diode (LED) or other source configured to effectuate tissue tightening, as will be described. The system 10 may be used to photochemically treat (and therefore tighten and/or lift) a target tissue 20 such as, but not limited to, skin, epidermis, dermis, fat, fascia, fascial membranes, tendon, epithelium, bladder, bowel, muscle, nervous, circulatory, abdominal, thoracic, colorectal, rectal, intestinal, ovarian, uterine, pericardial, peritoneal, oral, cardiac, and breast tissue, vaginal mucosa, superficial facial layers, superficial muscular aponeurotic system (SMAS), cooper's ligament, orbital septum, and fascia of scarpa. For example, the system 10 can be used to accomplish a breast tissue lift, a facial tissue lift, vaginal tightening, post-liposuction skin tightening, post bariatric weight loss surgery skin tightening, or other tissue tightening or lifting applications.

Figure 2:
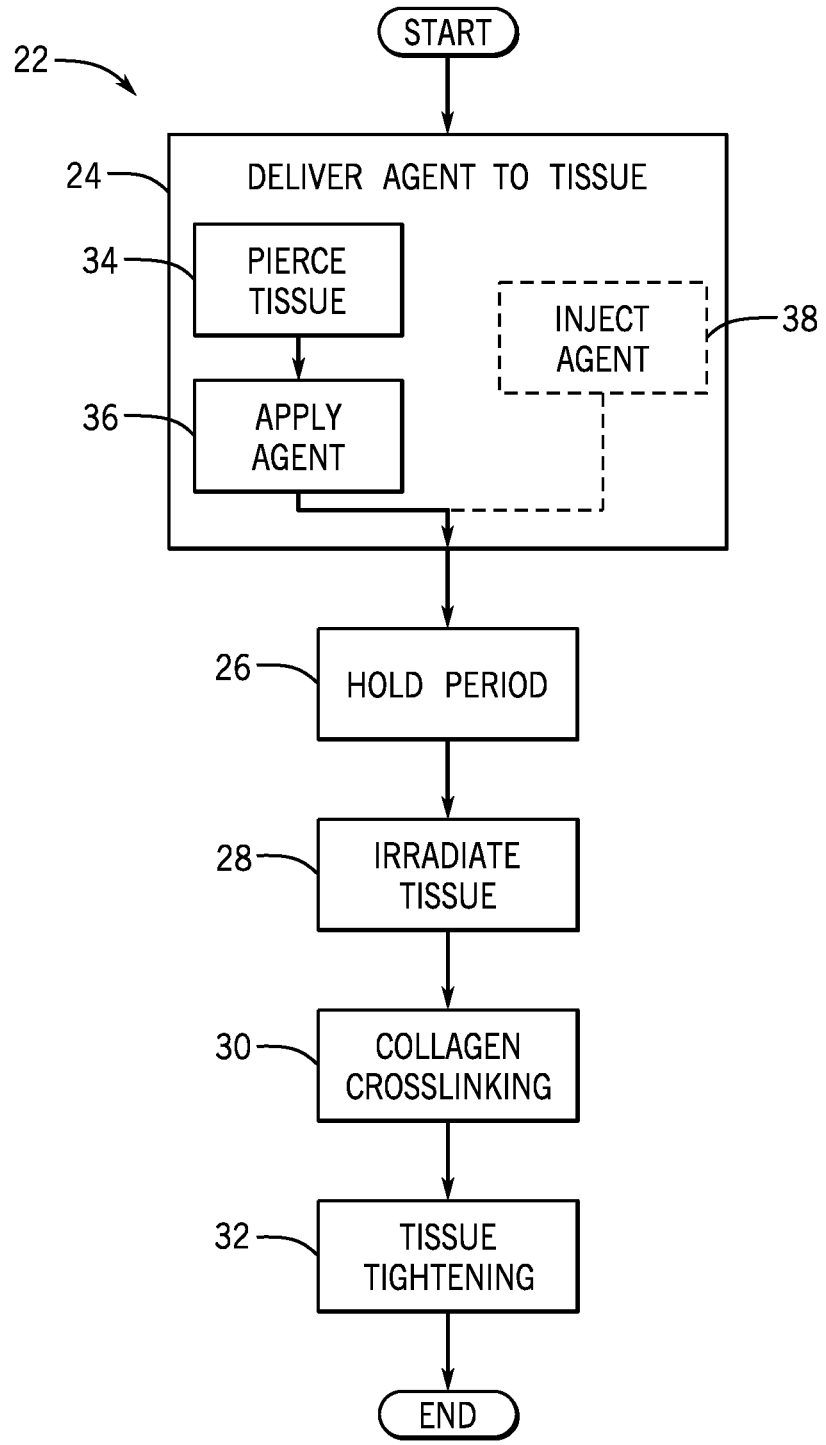
FIG. 2 is a flow diagram illustrating a method for tissue tightening.

The system 10 can be used to tighten the target tissue 20 according to the method 22 of FIG. 2. Generally, the method 22 may include a particular photochemical crosslinking (PXL) treatment of punctured target tissue 20. More specifically, the method 22 includes delivering a photochemical agent to the target tissue 20, for example, with the delivery mechanism 12 at process block 24. More particularly, as will be described, the delivery of the agent at process block 24 may include some substeps or may include one or more optional steps.

Once the agent is delivered to the tissue at process block 24, a hold period is observed at process block 26. Following the hold period at process block 26, the target tissue 20 is irradiated at process block 28. As one non-limiting example, the irradiation at process block 28 may be performed using the electromagnetic radiation source 18. In particular, as will be described, the irradiation at process block 28 is specifically performed to activate the photochemical agent delivered at process block 24 to cause, at process block 30, collagen crosslinking within the target tissue 20. The crosslinking causes the target tissue 20 to tighten or shrink at process block 32.

With respect to process block 24, the photochemical agent is delivered to the target tissue 20. As one example, delivery may be performed using the delivery mechanism 12 described above. Generally, a photochemical agent is a chemical compound that produces a chemical effect upon photoactivation or a chemical precursor of a compound that produces a chemical effect upon activation. For example, the photochemical agent may be a photosensitizer or photoactive dye. In one specific application, the photochemical agent can be Rose Bengal. In a further application, the photochemical agent can be 0.1% Rose Bengal in a saline solution. In other applications, the photochemical agent may be selected from the group consisting of xanthenes, flavins, thiazines, porphyrins, expanded porphyrins, chlorophylls, phenothiazines, cyanines, mono azo dyes, azine mono azo dyes, rhodamine dyes, benzophenoxazine dyes, oxazines, and anthroquinone dyes. In yet other applications, the photochemical agent may selected from the group consisting of Rose Bengal, erythrosine, riboflavin, methylene blue ("MB"), Toluidine Blue, Methyl Red, Janus Green B, Rhodamine B base, Nile Blue A, Nile Red, Celestine Blue, Remazol Brilliant Blue R, riboflavin-5-phosphate ("R-5-P"), N-hydroxypyridine-2-(I H)-thione ("N-HTP") and photoactive derivatives thereof.

The method 22 of FIG. 2 may include any of multiple options for delivering the photochemical agent. According to a first option, the photochemical agent can be applied by first puncturing or piercing a surface of the target tissue 20, for example with a needle 14 or an array of needles at process block 34. This initial needle puncturing creates access to tissue below the surface. More specifically, the initial need puncturing creates puncture holes to allow the photochemical agent to be delivered and distributed below a surface of the tissue 20 (that is, through the holes to a certain depth of the tissue), allowing collagen and other structural proteins within the tissue 20 (such as elastin) to be uniformly exposed to, surrounded by, coated by, in close proximity with, and/or adjacent the photochemical agent. Accordingly, needle puncture holes can be sufficiently spaced apart to puncture a certain percentage of tissue surface area. For example, in some applications, such as skin or epidermis tightening applications, the needle array can be used to puncture approximately less than ten percent or, preferably, five percent of the surface area of the target tissue 20.

Generally, the needle or needles 14 can be sized to pierce the tissue but not cause scarring. For example, in some applications, the needle 14 can be a hypodermic needle sized between 19 gauge and 30 gauge. In one specific example, the needle 14 can be 23 gauge. Coring needles or solid needles are also contemplated in some applications. The needle 14 can also be sized to penetrate a partial and/or a full thickness of the target tissue 20. The specific depth of the needle holes can be selected based on the target tissue type and location being treated. For example, hole depths of about 0.3 millimeters to 5 millimeters can be used in skin tissue, where such depths correspond approximately to the thickness of the dermis layer.

Figure 3:
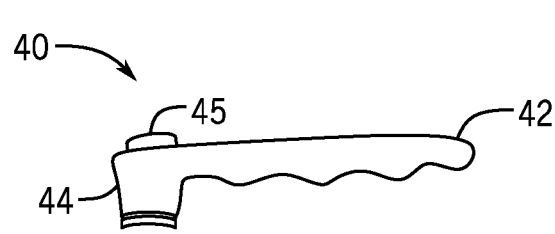
FIG. 3 is a side view of an example needle array for use with the system of FIG. 1.

Regarding needle arrays, both needle size and spacing can be configured to ensure proper distribution of the photochemical agent to a desired percentage of the tissue volume, without causing scarring. FIG. 3 shows an example needle array 40 that may be used in some applications. The needle array 40 can include a handle 42, a head 44, and a button 45. The handle 42 can be sized to permit a user to grip the handle 42. The head 44 can be integral with or coupled to an end of the handle 42 and can include retractable needles (not shown) configured to extend from a surface of the head 44 at an approximate 90-degree angle relative to the handle 42. The button 45 can be pushed or depressed to extend the retractable needles out from the head 44, and the needles can then again retract into the head 44 once a user stops depressing the button 45. The needles in the array 40 can have sizes similar to the hypodermic needles (or other needles) described above. In one application, the needle array 40 can include a set of hypodermic needle tips spaced approximately one millimeter apart in all directions. Other needle array configurations, besides what is shown in FIG. 3, is also contemplated in some applications. More specifically, the needle array 40 can be configured in any of a variety of spatial distributions depending on the tissue 20 being treated. For example, the needle array 40 can include multiple needles arranged as one or more rows, a regular two-dimensional pattern (such as a square, rectangular, or triangular pattern), a random distribution, or the like. Array configurations may also be sized and arranged based on desired direction of tissue lifting or tightening. Additionally, needle rollers or tattoo guns may be used in some implementations to puncture the target tissue 20.

Once the target tissue 20 is punctured, the photochemical agent is applied to a surface of the target tissue 20, for example using the applicator 16 at process block 36. The amount of photochemical agent applied to the target tissue 20 can depend on the type of target tissue 20 and, more specifically, the amount of collagen and other structure proteins in the target tissue 20. This application step can include, but is not limited to, staining, painting, brushing, spraying, dripping, or otherwise applying the photochemical agent to the target tissue 20. Example applicators 16 include, but are not limited to, sponges, brushes, and cotton tip applicators. According to another example, the applicator 16 can be a material, such as a bandage, with the photochemical agent soaked in, coated, or otherwise applied, so that the applicator 16 can be placed on the tissue 20 to transfer the photochemical agent to the tissue 20. Once the photochemical agent is applied to the target tissue 20 using one of the above-described methods, excess photochemical agent on the tissue surface may also be removed, for example by dabbing with gauze or another material.

According to a second application option, process blocks 34 and 36 can be consolidated or supplemented by directly injecting the photochemical agent into the tissue at process block 38. More specifically, a needle or needle array 14 can be inserted into the target tissue 20 and slowly drawn back out while simultaneously injecting the photochemical agent. By injecting the photochemical agent as the needle 14 is drawn out, collagen and other proteins in the target tissue 20 can be sufficiently surrounded by or in close proximity to the agent.

According to a third application option (not shown), the photochemical agent may be applied to a surface of the target tissue 20, and then the surface can be punctured with a tattoo gun to transfer the photochemical agent throughout a depth of the tissue 20 adjacent the proteins.

Following agent application, with respect to process block 26, a hold period can provide time for the photochemical agent to penetrate a depth of the target tissue 20 through the puncture holes in the target tissue 20 and surround, or be in very close proximity or adjacent to, the collagen. In some applications, the hold period can be about thirty seconds to about five minutes. In one specific application, the hold period is about one minute. An optimal hold period can be determined by experimental testing for specific target tissues and/or specific photochemical agents. For example, Rose Bengal has a high affinity for collagen and a relatively limited penetrance, thus requiring a minimal hold period.

Figure 4:
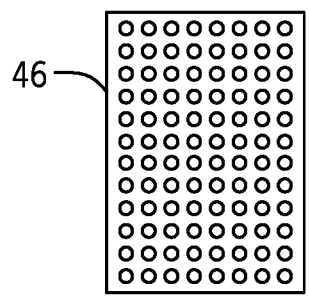
FIG. 4 is an underside view of an example light-emitting diode array for use with the system of FIG. 1.

With respect to process block 28, the target tissue 20 is irradiated, for example using the electromagnetic radiation source 18. The electromagnetic radiation source 18 can emit light at an appropriate energy, wavelength, and duration to cause photochemical agent activation. For example, the electromagnetic radiation source 18 can be configured to irradiate the target tissue at an irradiance of less than about one watt per centimeter squared (W/cm$^2$). In other applications, however, light can be delivered at an irradiance between about 0.5 W/cm$^2$ to about five W/cm$^2$, preferably between about one W/cm$^2$ and about three W/cm$^2$. Also, the electromagnetic radiation source 18 can be a low-energy visible-light emitter, for example, configured to emit monochromatic or polychromatic light. Suitable electromagnetic radiation source examples include, but are not limited to, commercially available lasers, lamps, one or more light-emitting diodes ("LEDs"), or other sources of electromagnetic radiation. In one specific example, the electromagnetic radiation source 18 can be a multi-light-emitting LED array 46, as shown in FIG. 4. More specifically, the LED array 46 can be a high-powered (300 milliwatt) LED array.

Furthermore, the electromagnetic radiation source 18 can emit light at an appropriate wavelength that activates the type of photochemical agent used. More specifically, the wavelength of light can be chosen so that it corresponds to or encompasses the absorption of the photochemical agent, and reaches a desired volume of tissue 20 that has been contacted with the photochemical agent (that is, penetrates a desired depth of the tissue 20). For example, when Rose Bengal is the photochemical agent used, the electromagnetic radiation source 18 can be a low-energy, green-light emitter. For other photochemical agents, the wavelength used can range from about 350 nanometers to about 800 nanometers, preferably between about 400 nanometers to about 700 nanometers.

Also, the electromagnetic radiation source 18 can emit light at the target tissue 20 for an appropriate duration based on the photochemical agent and tissue type. In some applications, the target tissue 20 is irradiated for a duration of about one minute to about thirty minutes. In other applications, the target tissue 20 is irradiated for a duration of less than about five minutes.

Moving on to process block 30, irradiating the target tissue 20 with the electromagnetic radiation source 18 activates the photochemical agent, causing collagen cross-linking. More specifically, when distributed adjacent to collagen, the photochemical agent binds to the collagen in a noncovalent manner. The illumination then activates the photochemical agent to induce collagen crosslinking through covalent bonding. Furthermore, while other structural proteins like elastin may not have the same physical interaction with the photochemical agent as collagen, the other proteins may still experience the same protein response to the illumination as collagen.

At process block 32, the effect of crosslinking is that the target tissue 20 is tightened (that is, the tissue volume is reduced). In other words, the activated photochemical agent causes a protein response that brings fibers of the tissue closer together in order to tighten the tissue or reduce tissue laxity. For example, target skin tissue 20 treated using the above method 22 becomes stronger and more resistant to degradation typically seen with aging. Specifically, the collagen crosslinking inhibits the ability of matrix metalloproteinase ("MPPs," also known as fibroblast collagenase) to breakdown collagen, slowing the aging process and the appearance of cellulite. In other words, the collagen crosslinking tightens the skin, hiding the appearance of cellulite and protecting against dermal thinning—one of the major causes of cellulite. In another example, in the case of target face or breast tissue 20, tightening the tissue 20 via the above method can lift the tissue 20 (therefore providing a face lift or a breast lift).

In addition to the above-described method, other methods may be used to transdermally deliver the photochemical agent to the target tissue 20 in some implementations. For example, a separate electromagnetic radiation source, such as a laser, can be used to create the holes (that is, rather than the needle 14). In another example, when the target tissue 20 is skin, the stratum cornea (that is, the outermost layer of the epidermis) can be removed by tape, Jessners solution, Trichloroacetic Add, or another chemical agent or solution. In other words, the surface of the target tissue 20 can be "punctured" by removing its outermost layer. Following this removal step, the photochemical agent can be applied to the tissue 20, as described above. Additionally, liposomes or other nano-carriers may be used to deliver the photochemical agent so that it surrounds the target tissue 20. For example, a nano-carrier with the photochemical agent can be delivered to the surface of the target tissue 20 so that the nano-carrier penetrates the target tissue 20 to distribute the photochemical agent adjacent the proteins within the tissue 20. Other nanotechnology techniques may also be used.

Because of the needling step (process block 34) and/or the injection step (process block 38), a depth of the tissue 20—rather than just the tissue surface—can receive the photochemical agent subjected to irradiation. In some applications, only applying a photochemical agent to the tissue surface does not allow collagen to be coated by the agent or sufficiently irradiated to activate collagen crosslinking. For example, certain photochemical agents have limited penetration through the superficial skin barrier and cannot reach into the tissue to allow for collagen crosslinking. As a result, such photochemical agents are not effective without intentionally creating holes in the tissue 20 (via process blocks 34 or 38) to receive the photochemical agent.

Thus, unlike previous photochemical treatment therapies, which serve to close tissue holes or wounds, the present method 22 intentionally creates holes in the tissue 20 in order to tighten it. In particular, unlike previous therapies, the present photochemical crosslinking method 22 applies a photochemical agent and light to a tissue 20 to crosslink proteins to bring structural fibers closer together to reduce the tissue volume and therefore tighten it. For example, photochemical tissue bonding involves crosslinking between two tissue surfaces to bond the separate tissue surfaces together, and photochemical tissue passivation involves crosslinking a single tissue surface to modify a biological response (such as to strengthen or stiffen the tissue). Unlike photochemical bonding or tissue passivation, which treat two tissues and a tissue surface, respectively, the present photochemical crosslinking method is used to treat a volume of tissue (that is, from the tissue surface through a depth of the tissue) to tighten the tissue and reduce laxity. In other words, the other methods do not cause the same response as the present method, that is, bonding or strengthening tissues using the other methods does not cause a reduction in tissue volume or laxity.

Figure 5:
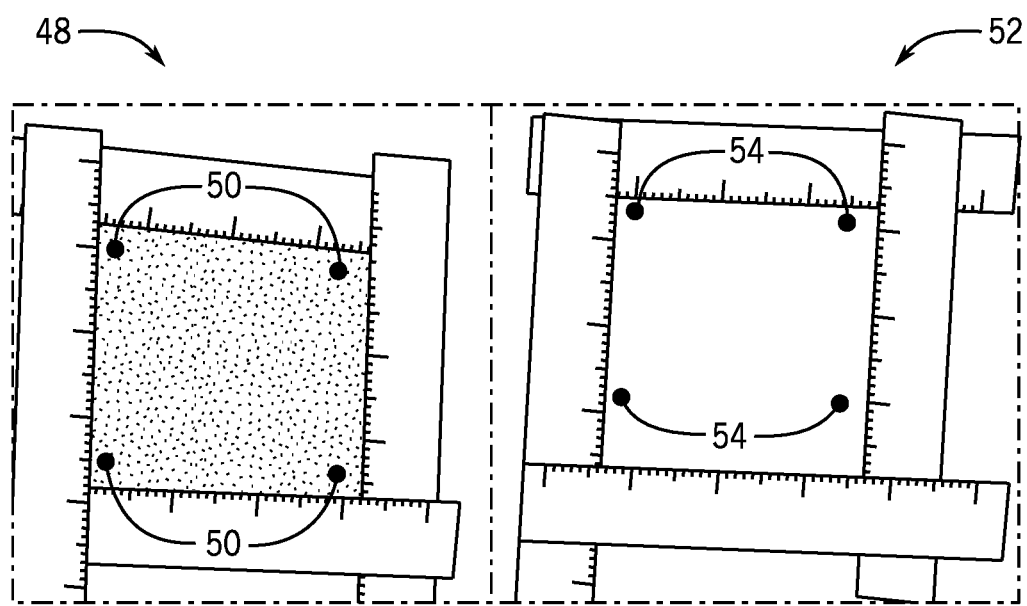
FIG. 5 illustrates photographs comparing an untreated tissue sample to a tissue sample treated using the method of FIG. 2.

By way of example, the above-described system 10 and method 22 were experimentally used for photochemically tightening human skin of five patients (discarded from elective abdominoplasty operations). Of the twenty-six sample sites treated, on average, the total surface area of treated samples decreased by 6% ($p<0.001$). For example, FIG. 5 illustrates a comparison between a sample before treatment 48, including reference markers 50, and after treatment 52, including reference markers 54. As shown in FIG. 5, the reference markers 54 of the post-treatment sample 52 are closer together than the reference markers 50 of the pre-treatment sample 48, illustrating a decrease in tissue surface area caused by the treatment.

Additionally, mechanical testing was performed on sample sites using a tensiometer to measure elastic modulus before and after treatment. The elastic modulus and peak load were recorded on samples that were (1) untreated (2) partially treated (needled only), and (3) fully treated (needled plus agent application and irradiation). Full treatment included full thickness needling of the skin surface followed by application of a 0.1% solution of Rose Bengal in saline and irradiation with a multi-light-emitting LED diode array that delivered green light to the sample surface. In comparing the three test groups, there was no statistically significant difference between untreated skin and needled skin; however, there was a statistical difference between those two groups and photochemically-treated samples, with the latter exhibiting a five-fold increase in the elastic modulus and a three-fold increase in peak load.

Furthermore, a biodegradation assay was performed to assess the efficacy of the above method 22 to inhibit collagenase breakdown of collagen (collagenase is an enzyme that breaks down, or digests, collagen). The assay was performed to compare an untreated (control) group and a treated group. For the control group, the digestion time was 180 minutes. For the treated group, the digestion time was 420 minutes. This represents a 2.3-fold increase in the time needed for digestion, thus showing that the treatment (using the above method 22) does, in fact, inhibit collagen biodegradation due to crosslinking.

Accordingly, the system 10 and the method 22 can decrease tissue surface area, increase elastic modulus, increase peak load, and/or increase collagenase digestion time. For example, compared to untreated tissue, the system 10 and method 22 can decrease tissue surface area by between about 1% to about 40%, preferably between about 5% to about 25%; can increase elastic modulus between about two-fold to about twenty-fold, preferably between about four-fold to about ten-fold; can increase peak load between about two-fold to about ten-fold, preferably between about two-fold to about five-fold; and can increase collagenase digestion time between about two-fold to about ten-fold, preferably between about two-fold to about five-fold. Other ranges of decreased surface area and increase elastic module, peak load, and/or digestion time are also contemplated.

In light of these advantages, the system 10 and method 22 can be used in applications such as those related to reducing skin laxity; body contouring; skin tightening of aged, post-surgical, or post-liposuction skin; non-surgical breast lifts or face lifts; vaginal tightening; reducing the appearance of cellulite or striae (that is, stretch marks); or tightening tissues like lose tendons. Other applications are also contemplated.

When used for such applications, the above system 10 and method 22 provide a minimally invasive treatment. Thus, the system 10 and method 22 provide a safer, less risky, and more efficient way to tighten tissue compared to surgery. The method 22 also provides for shorter recovery times and fewer complications than other aesthetic treatments, such as Thermage® (a radiofrequency energy treatment), Ultherapy® (an ultrasound energy treatment), fractional ablative lasers (a treatment that removes a layer of tissue), and coring needles (a treatment that punctures tissue to remove small tissue biopsies).

More specifically, compared to other energy-based treatments, the method 22 is fluence dependent. The method 22 is therefore a safer, more forgiving, and a less painful alternative to power-dependent systems, such as ablative lasers. Also, the present method 22 does not cause a substantial temperature increase in the tissue 20 compared to other energy-based treatments. For example, ultrasound- and radiofrequency-based methods do not cause crosslinking, but rather thermally injure tissue to induce tissue remodeling and contracture. Unlike those thermal methods, the present method 22 does not heat the tissue 20 enough to cause damage, and therefore preserves the tissue's structural integrity by preventing cell toxicity and avoiding protein denaturation due to tissue heating.

Additionally, the photochemical skin tightening system 10 and method 22 has been shown to deliver consistent, natural-looking results with long-lasting effects. In particular, the system 10 and method 22 have been shown to be more consistent than other surgery alternatives, and have shown similar, consistent results for all types of tissue treated. Furthermore, the results are more natural-looking because the system 10 and method 22 do not leave any scars (e.g., due to surgical cutting or thermal damage).

The system 10 and method 22 may also be more affordable than current treatments. In particular, because the system 10 and method 22 are a surgery alternative, treatment can be performed by, for example, a nurse practitioner in a clinic or physician's office rather than a surgeon in an operating room. And the system 10 and method 22 do not require costly capital equipment, like the laser-emitters required for other surgery alternatives, but still produce a high-margin consumable. For example, the system 10 and, in particular, the electromagnetic radiation source 18 may be cheaper than and occupy a smaller footprint than traditional ablative lasers.

Figure 6:
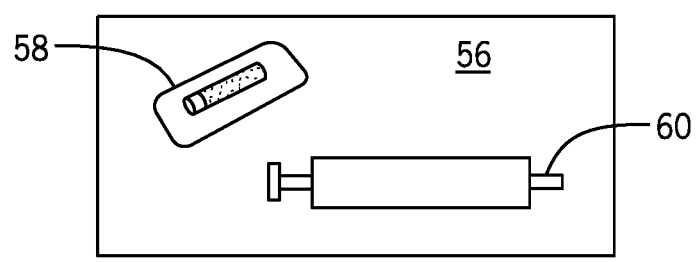
FIG. 6 is a schematic view of a tissue tightening system kit.

In some applications, the electromagnetic radiation source 18 (such as a laser) can be easily stored in a clinical setting, and a photochemical treatment kit 56, as shown in FIG. 6, can be provided for use with the electromagnetic radiation source 18. The kit 56 can include an agent 58 and a needle device 60 (such as a single hypodermic, solid, or coring needle 14 or a needle array 40). Alternatively, the kit 56 can include an agent 58 and a disposable head 44 (as shown in FIG. 3) for use with a reusable handle 42, which can be stored in a clinic setting. In yet other applications, the kit 56 can further include one or more applicators. Also, the kit 56 can be scalable for different treatment areas or tissues. For example, the amount of agent 58 and the size of the needle device 60 in each kit 56 can be specific to a treatment area or tissue.

The present invention has been described in terms of one or more preferred embodiments, and it should be appreciated that many equivalents, alternatives, variations, and modifications, aside from those expressly stated, are possible and within the scope of the invention. Furthermore, the term "about" as used herein means a range of plus or minus 20% with respect to the specified value, more preferably plus or minus 10%, even more preferably plus or minus 5%, most preferably plus or minus 2%. In the alternative, as known in the art, the term "about" indicates a deviation, from the specified value, that is equal to half of a minimum increment of a measure available during the process of measurement of such value with a given measurement tool.

The invention claimed is:

1. A kit for treating tissue and for use with an electromagnetic radiation source, the kit comprising:
   a needle sized to create puncture holes in the tissue; and
   a photochemical agent configured to penetrate through the puncture holes when applied to the tissue and to be activated to cause crosslinking of proteins in the tissue when irradiated with a predetermined electromagnetic radiation by the electromagnetic radiation source following a predetermined time period,
      wherein the predetermined electromagnetic radiation is at a wavelength that activates the photochemical agent, causing a protein response that brings fibers through a depth of the tissue closer together in order to one of reduce tissue laxity and tighten the tissue,
      wherein the predetermined time is selected to enable the photochemical agent to penetrate the depth of the tissue and become distributed adjacent proteins within the tissue,
   wherein the predetermined time period is between about thirty seconds to about five minutes, and
   wherein the needle is part of a needle array comprising: a head with internal needles extendable from a surface of the head by a button, the head configured to be coupled to a separate handle, wherein the needle is configured to simultaneously inject the photochemical agent through the needle while being pulled from the tissue so that the photochemical agent penetrates a depth of the tissue.

2. The kit of claim 1, wherein the needle includes one of a single needle and a needle array.

3. The kit of claim 1, further comprising an applicator to deliver the photochemical agent to the tissue, and wherein the applicator is one of a sponge, a brush, a cotton tip applicator, and a bandage.

4. The kit of claim 1, wherein the needle array includes multiple needles arranged in one of a plurality of rows, a square pattern, a rectangular pattern, a triangular pattern, or a random distribution pattern.

5. The kit of claim 1, wherein the needle is one of a hypodermic needle, a solid needle, or a coring needle sized between 19 gauge to 30 gauge.

6. The kit of claim 1, wherein the photochemical agent is one of Jessner's solution or Trichloroacetic Acid.

7. The kit of claim 1, wherein the needle is part of a tattoo gun.

8. The kit of claim 1, wherein the electromagnetic radiation source is configured to deliver an irradiance of less than about one watt per centimeter squared.

9. The kit of claim 1, wherein the electromagnetic radiation source is configured to deliver an irradiance with a wavelength between about 350 nanometers to about 800 nanometers.

10. The kit of claim 1, wherein the photochemical agent is one of a xanthene, a flavin, a thiazine, a porphyrin, an expanded porphyrin, a chlorophyll, a phenothiazine, a cyanine, a mono azo dye, an azine mono azo dye, a rhodamine dye, a benzophenoxazine dye, an oxazine, an anthroquinone dye, Rose Bengal, erythrosine, riboflavin, methylene blue, Toluidine Blue, Methyl Red, Janus Green B, Rhodamine B base, Nile Blue A, Nile Red, Celestine Blue, Remazol Brilliant Blue R, riboflavin-5-phosphate, or Nhydroxypyridine-2-(I H)-thione.

11. The kit of claim 1, wherein the electromagnetic radiation source includes at least one of a laser, a lamp, a light-emitting diode, or a light-emitting diode array.

12. The kit of claim 1, wherein the proteins include at least one of collagen or elastin.

13. The kit of claim 1, wherein the tissue includes one of skin, epidermis, dermis, fat, fascia, fascial membranes, tendon, epithelium, bladder tissue, bowel, muscle tissue, nervous tissue, circulatory tissue, abdominal tissue, thoracic tissue, colorectal tissue, rectal tissue, intestinal tissue, ovarian tissue, uterine tissue, pericardial tissue, peritoneal tissue, oral tissue, cardiac tissue, breast tissue, vaginal mucosa, superficial facial layers, superficial muscular aponeurotic system, cooper's ligament, orbital septum, or fascia of scarpa.

14. The kit of claim 1, wherein the electromagnetic radiation source is configured to deliver irradiation configured to cause a protein response that accomplishes one of a breast tissue lift, a facial tissue lift, vaginal tightening, post liposuction skin tightening, or post bariatric weight loss surgery skin tightening.

* * * * *

UNITED STATES PATENT AND TRADEMARK OFFICE
CERTIFICATE OF CORRECTION

PATENT NO. : 11,883,680 B2
APPLICATION NO. : 17/660536
DATED : January 30, 2024
INVENTOR(S) : Michael McCormack et al.

Page 1 of 1

It is certified that error appears in the above-identified patent and that said Letters Patent is hereby corrected as shown below:

In the Specification

Column 6, Line 56, "Add" should be --Acid--.

Signed and Sealed this
Twenty-third Day of April, 2024

Katherine Kelly Vidal
*Director of the United States Patent and Trademark Office*